United States Patent
Nuckolls et al.

(10) Patent No.: US 9,856,281 B2
(45) Date of Patent: Jan. 2, 2018

(54) SOLID-STATE MATERIALS FORMED OF MOLECULAR CLUSTERS AND METHOD OF FORMING SAME

(71) Applicant: The Trustees of Columbia University in the City of New York, New York, NY (US)

(72) Inventors: Colin Nuckolls, New York, NY (US); Michael Louis Steigerwald, Martinsville, NJ (US); Xavier Roy, Brooklyn, NY (US); Philip Kim, New York, NY (US); Chulho Lee, New York, NY (US); Seok Ju Kang, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 218 days.

(21) Appl. No.: 14/474,972

(22) Filed: Sep. 2, 2014

(65) Prior Publication Data
US 2016/0024128 A1    Jan. 28, 2016

Related U.S. Application Data

(63) Continuation of application No. PCT/US2013/031024, filed on Mar. 13, 2013.
(Continued)

(51) Int. Cl.
*H01B 1/06* (2006.01)
*C07F 15/00* (2006.01)
(Continued)

(52) U.S. Cl.
CPC .............. *C07F 15/06* (2013.01); *B82Y 10/00* (2013.01); *C01B 19/007* (2013.01); *C07F 11/00* (2013.01); *C07F 15/04* (2013.01); *H01B 1/121* (2013.01); *C01P 2002/72* (2013.01); *C01P 2002/76* (2013.01); *C01P 2002/77* (2013.01);
(Continued)

(58) Field of Classification Search
CPC .... H01B 1/00; H01B 1/04; H01B 1/06; C01B 17/00; C01B 19/007; C01B 31/0213
See application file for complete search history.

(56) References Cited

U.S. PATENT DOCUMENTS 5,324,495 A  *  6/1994  Gorun ................... B82Y 30/00
                                               252/500
7,473,650 B2      1/2009  Rantala et al.
(Continued)

OTHER PUBLICATIONS

Yuan et al "W6S8 Inorganic Clusters with Organic TTF Derivative Ligands: in Pursuit of Multidimensional Conductive Networks" Chem. Mater. 2006, 18, 4296-4306.*
Saito et al "Synthesis of [Mo6S8(PEt3)6] by reductive dimerization of a trinuclear molybdenum chloro sulfido cluster complex coordinated with triethylphosphine and methanol: a molecular model for superconducting Chevrel phases" J. Am. Chem. Soc. 1988, 110, 1646-1647.*
(Continued)

*Primary Examiner* — Mark Kopec
(74) *Attorney, Agent, or Firm* — Baker Botts L.L.P.

(57) ABSTRACT

A solid-state material comprising a solid-state compound is provided. The solid-state compound has the formula: [Cluster1][Cluster2]$_n$, where Cluster1 can be a metal chalcogenide molecular cluster, Cluster2 a carbon cluster, and n the number of Cluster2 clusters in the solid-state compound. A method of forming a solid-state material is also provided.

28 Claims, 10 Drawing Sheets

Related U.S. Application Data

(60) Provisional application No. 61/618,237, filed on Mar. 30, 2012.

(51) Int. Cl.

| | | |
|---|---|---|
| *C07F 15/06* | (2006.01) | |
| *C01B 19/00* | (2006.01) | |
| *B82Y 10/00* | (2011.01) | |
| *C07F 11/00* | (2006.01) | |
| *C07F 15/04* | (2006.01) | |
| *H01B 1/12* | (2006.01) | |
| *H01L 51/00* | (2006.01) | |

(52) U.S. Cl.
CPC ...... *C01P 2002/78* (2013.01); *C01P 2002/82* (2013.01); *C01P 2002/84* (2013.01); *C01P 2004/02* (2013.01); *C01P 2004/03* (2013.01); *C01P 2006/32* (2013.01); *C01P 2006/42* (2013.01); *H01L 51/0046* (2013.01)

(56) References Cited

U.S. PATENT DOCUMENTS

| | | | |
|---|---|---|---|
| 7,643,717 | B2 | 1/2010 | Rantala et al. |
| 7,928,432 | B2 | 4/2011 | Nuckolls et al. |
| 8,124,179 | B2 | 2/2012 | Nilsen et al. |
| 2004/0081887 | A1 | 4/2004 | Sugiyama et al. |
| 2007/0274895 | A1 | 11/2007 | Jesih et al. |
| 2008/0300323 | A1 | 12/2008 | Caldwell et al. |
| 2010/0143693 | A1 | 6/2010 | Yaghi et al. |
| 2010/0172823 | A1 | 7/2010 | Tenne et al. |
| 2011/0017979 | A1 | 1/2011 | Meric et al. |
| 2011/0275062 | A1 | 11/2011 | Guo et al. |

OTHER PUBLICATIONS

Brown et al "Quantum Dot Solar Cells. Electrophoretic Deposition of CdSe—C60 Composite Films and Capture of Photogenerated Electrons with nC60 Cluster Shell", J. Am. Chem. Soc. 2008, 130, 8890-8891.*

Kang et al "Integrity and Structural Characteristics of the M6E8 (E=S, Se, Te) Cluster Core: Syntheses and Structures of [Co6S8(PR3)6]n+ (R=Me2Ph, n=1; R=OMe, n=0)" Journal of Cluster Science, vol. 10, No. 3, 1999 (pp. 429-443).*

Liu et al "Chemical conjugation of fullerence C60 to CdSe nanocrystals via dithiocarbamate ligands", J. Phys. Chem. C 2007, 111, 17713-19.*

Chase et al "Substituted C60 Molecules: A study in symmetry reduction" J. Am. Chem. Soc. 1992, 114, 2252-56.*

Goddard et al "Synthesis and Characterization of Four Consecutive Members of the Five-Member [Fe6S8(PEt3)6]n+ (n=0-4) Cluster Electron Transfer Series" Inorg. Chem. 1996, 35, 4347-54.*

Lightcap et al "Fortification of CdSe Quantum Dots with Graphene Oxide. Excited State Interactions and Light Energy Conversion", J. Am. Chem. Soc., 2012, 134 (16), pp. 7109-7116.*

Roy et al "Nanoscale Atoms in Solid-State Chemistry", Science, 34, (Jul. 2013) pp. 157-160.*

Popescu, M. et al., "Nanocarbon Embedded Chalcogenides, Onion-Like Model. *Journal of Optoelectronics and Advanced Materials*", Nov.-Dec. 2011, vol. 13, Nos. 11-12, p. 1451, right column.

Russo, M. et al., "One-pot synthesis of polymer/inorganic hybrids: toward readily accessible, low-loss, and highly tunable refractive index materials and patterns", *Polymer Physics*, vol. 50/Issue 1, pp. 65-74, (pub date) Oct. 2011.

International Search Report dated May 28, 2013 in PCT/US13/31024.

* cited by examiner

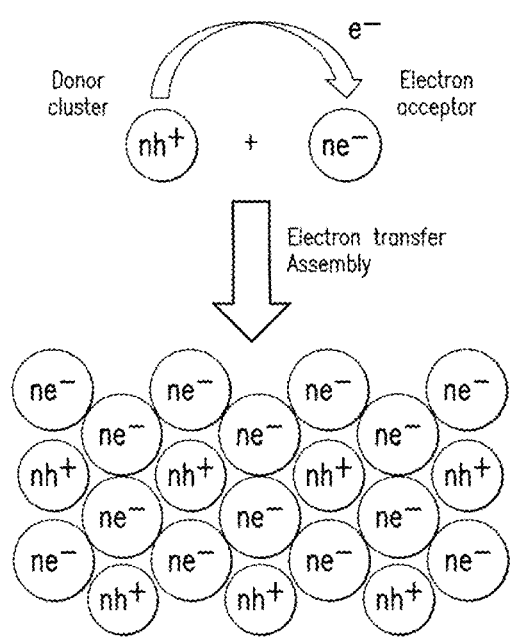
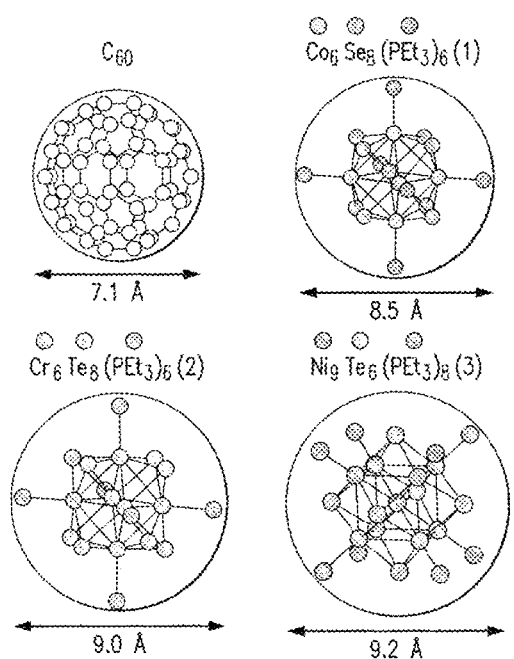
FIG. 1A
FIG. 1B

SOLID-STATE MATERIALS FORMED OF MOLECULAR CLUSTERS AND METHOD OF FORMING SAME

CROSS-REFERENCE TO RELATED APPLICATIONS

This application is a continuation of PCT/US13/031024, filed Mar. 13, 2013, which claims priority to U.S. Provisional Patent Application Ser. No. 61/618,237, filed on Mar. 30, 2012, which is incorporated by reference herein in its entirety.

STATEMENT REGARDING FEDERALLY-SPONSORED RESEARCH

This invention was made with government support under grant DE-SC0001085, awarded by the EFRC. The government has certain rights in the invention.

BACKGROUND

The disclosed subject matter relates to solid-state materials, which can be used, for example, in electronic devices.

Many popular electronic devices such as computers and cellular phones rely on semiconductors made of inorganic silicon, which can require multiple and costly steps to produce. Recently, inorganic-organic hybrid materials have been prepared, which have the potential to exhibit high carrier mobility found in inorganic semiconductors, while maintaining the processing simplicity found in organic synthesis.

The chemistry of molecular clusters is well developed with a wide variation in the size and composition of the clusters that have been synthesized. Despite their ready availability, molecular clusters have seldom been used in electronic materials due to the insulating ligands that typically passivate the exterior of the clusters.

Thus, there is a need for a more readily made material that can be used in electronic devices as an alternative to purely inorganic materials, e.g., silicon.

SUMMARY

Solid-state materials and methods of forming same are provided herein.

According to one aspect of the disclosed subject matter, a solid-state material is provided using a solid-state compound. The solid-state compound has the formula [Cluster1][Cluster2]$_n$, where Cluster1 can be a metal chalcogenide molecular cluster, Cluster2 a carbon cluster, and n the number of Cluster2 clusters in the solid-state compound.

In some embodiments, Cluster1 can be $Co_6Se_8(PEt_3)_6$, Cluster2 can be $C_{60}$ and n can be 2. The solid-state material can be assembled into a superatomic relative of a $CdI_2$ structure, and/or include hexagonal arrays of $C_{60}$ in a chair-like arrangement that is separated by layers of the $Co_6Se_8(PEt_3)_6$ clusters.

The solid-state material can include at least two $C_{60}$ layers spaced apart by about 12.5 Å. The solid-state material can include at least two $C_{60}$s having a centroid-to-centroid distance about 9.9 Å and a shortest non-bonded C—C spacing of about 3.4 Å. Each $Co_6Se_8(PEt_3)_6$ cluster can transfer two electrons and each $C_{60}$ cluster can receive one electron. The solid state material can have a thermal activation energy of about 150 meV.

In some embodiments, Cluster1 can be $Cr_6Te_8(PEt_3)_6$, Cluster2 can be $C_{60}$ and n can be 2. The solid-state material can include at least two $C_{60}$ layers spaced apart by about 12.3 Å. The solid-state material can include at least two $C_{60}$s having a centroid-to-centroid distance about 10.3 Å and a shortest non-bonded C—C spacing of about 3.7 Å. Each $Cr_6Te_8(PEt_3)_6$ cluster can transfer two electrons and each $C_{60}$ cluster can receive one electron. The solid state material can have a thermal activation energy of about 100 meV.

In some embodiments, Cluster1 can be $Ni_9Te_6(PEt_3)_8$, Cluster2 can be $C_{60}$ and n can be 1. The solid-state material can be assembled into a rock-salt crystal structure or a face centered cubic structure. The cubic structure can have a lattice parameter of about 21.7 Å.

In some embodiments, the solid-state material can be used in an electronic material, such as a flexible electronic material.

A method of forming a solid-state material is also provided. An example method includes dissolving a metal chalcogenide molecular cluster in toluene, dissolving a carbon cluster in toluene, and combining the metal chalcogenide molecular cluster and the carbon cluster to form a solid-state material.

In some embodiments, the method can further include decanting a supernatant after combining the metal chalcogenide molecular cluster and the carbon cluster, washing a remaining solid with toluene after decanting, and/or drying the remaining solid under vacuum after washing, e.g., for about 12 hours.

BRIEF DESCRIPTION OF THE DRAWINGS

FIG. 1A is a diagram illustrating electron transfer assembly of binary cluster solids in accordance with one aspect of the disclosed subject matter.

FIG. 1B includes diagrams illustrating the structures of the $C_{60}$, $Co_6Se_8(PEt_3)_6$, 2, and $Ni_9Te_6(PEt_3)_8$ molecular building blocks in accordance with one aspect of the disclosed subject matter.

DETAILED DESCRIPTION

Figure 2A:
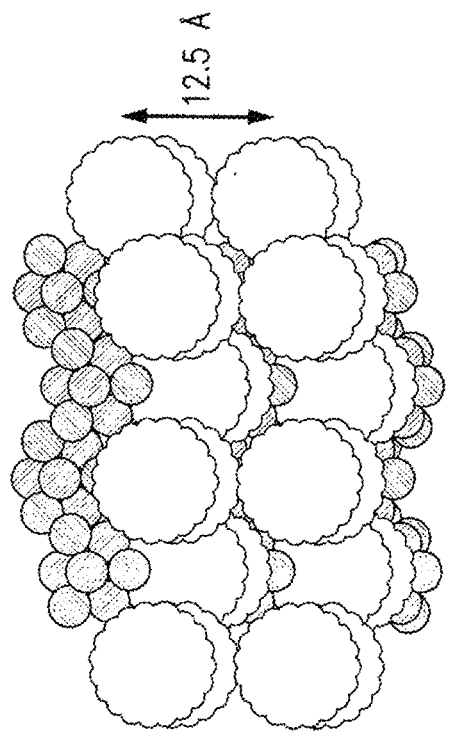
FIGS. 2A and 2B are diagrams illustrating the space filling molecular structure of $Co_6Se_8(PEt_3)_6.2C_{60}$ showing the crystal packing looking down the c-axis (for FIG. 2A) and the ab-plane (for FIG. 2B).

One aspect of the disclosed subject matter relates to solid-state materials formed of molecular clusters. The disclosed subject matter can be used for a variety of applications such as, for example and without limitation, electronic materials including flexible electronic materials such as displays, piezoelectrics, magnetics, semiconductors, photovoltaics, electrically insulating materials, sensors for pressure, gas, temperature, and magnetic fields, coatings, passivation materials, glob top materials, underfill materials, materials for IC, micro-lenses, optical devices, and the like.

The solid-state material can be formed from a binary assembly of atomically precise quantum dots, which can be tunable molecular cluster superatom building blocks. The solid-state material can be an organic-inorganic hybrid material. The solid-state material can include a solid-state compound having the formula [Cluster1][Cluster2]$_n$. Cluster1 can be a metal chalcogenide molecular cluster, such as but not limited to $Co_6Se_8(PEt_3)_6$, $Cr_6Te_8(PEt_3)_6$, or $Ni_9Te_6(PEt_3)_8$. Cluster2 can be a carbon cluster such as a fullerene, e.g., $C_{60}$. n is the number of Cluster2 clusters in the solid-state compound. Exemplary solid-state compounds include, but are not limited, to $[Co_6Se_8(PEt_3)_6][C_{60}]_2$, $[Cr_6Te_8(PEt_3)_6][C_{60}]_2$, and $[Ni_9Te_6(PEt_3)_8][C_{60}]$.

Conventional binary solid-state compounds, i.e., $A_xB_y$, are infinite, crystalline arrays of atoms A and B. The disclosed subject matter provides analogous binary solids in which the building blocks are molecular clusters rather than simply atoms. The solid-state materials can be prepared by combining independently synthesized molecular clusters. While the internal structures of the constituent clusters remain unchanged, charge can be transferred between them such that the resulting solids can be viewed as ionic solids in the same way that, for example, $CdI_2$ and NaCl are ionic solids.

The solid-state compounds in accordance with the disclosed subject matter have properties that are a consequence of the structure and coupling of the individual superatom components. The molecular cluster building blocks can be engineered and their electronic and structural complementarity can be tuned to four atomically precise binary assemblies in the solid-state. Charge transfer between the molecular clusters in the assembly can create highly conductive and magnetically ordered networks. For the purpose of illustration and not limitation, FIG. 1A shows a schematic representing electron transfer assembly of binary cluster solids.

For the purpose of illustration and not limitation, FIG. 1B show the structures of the exemplary $C_{60}$, $Co_6Se_8(PEt_3)_6$, $Cr_6Te_8(PEt_3)_6$, and $Ni_9Te_6(PEt_3)_8$ molecular building blocks as measured by single crystal X-ray diffraction. In the figure, the clusters are depicted on the same size scale. The diameter of the cluster is determined as the long diagonal P—P distance. The ethyl groups on the phosphines of the metal chalcogenide molecular cluster were removed to clarify the view.

In accordance with one aspect of the disclosed subject matter, constituent molecular clusters that have the same, approximately spherical, shape but very different electronic properties can be used in order to encourage reaction and subsequent structural association. By analogy to atomic solid-state chemistry, the in situ transfer of charge can produce ions (or the equivalent) that can form an ordered solid. Cluster pairs in which one cluster is relatively electron-poor and the other is relatively electron-rich can be used. For example, $C_{60}$ carbon clusters are good electron acceptors and the electrically neutral metal chalcogenide clusters, e.g., $Co_6Se_8(PEt_3)_6$, $Cr_6Te_8(PEt_3)_6$, and $Ni_9Te_6(PEt_3)_8$, are all electron-rich. These clusters (as shown in FIG. 1B) can be similar in size and shape to the fullerene.

Figure 2B:
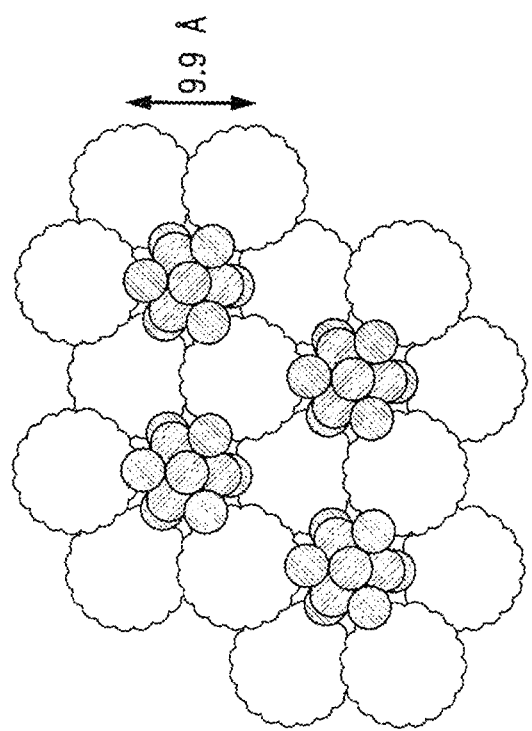

In accordance with one aspect of the disclosed subject matter, cluster $Co_6Se_8(PEt_3)_6$ can be combined with two equivalents of $C_{60}$ in toluene. Crystals can form immediately. In one exemplary embodiment, after waiting about 12 hours, black crystals can be obtained. Single crystal X-ray diffraction (SCXRD) indicates that this crystalline solid is a 1:2 stoichiometric combination of $Co_6Se_8(PEt_3)_6$ and $C_{60}$ (i.e., $Co_6Se_8(PEt_3)_6 \cdot 2C_{60}$). For the purpose of illustration and not limitation, FIGS. 2A and 2B show the space filling molecular structure of $Co_6Se_8(PEt_3)_6 \cdot 2C_{60}$ showing the crystal packing looking down the c-axis (for FIG. 2A) and the ab-plane (for FIG. 2B). In FIGS. 2A and 2B, carbon is black, phosphorus is orange, and selenium is green. As shown, the structure is composed of hexagonal arrays of $C_{60}$'s in a chair-like arrangement that is separated by layers of the $Co_6Se_8(PEt_3)_6$ clusters. In an exemplary embodiment, the $C_{60}$ layers can be about 12.5 Å apart, and/or the centroid-to-centroid distance and the shortest non-bonded C—C spacing between two adjacent $C_{60}$'s can be about 9.9 Å and 3.4 Å, respectively. These distances are comparable to crystalline $C_{60}$. Different packing can provide different dimensions, and different sized components can provide different spacings.

Figure 3:
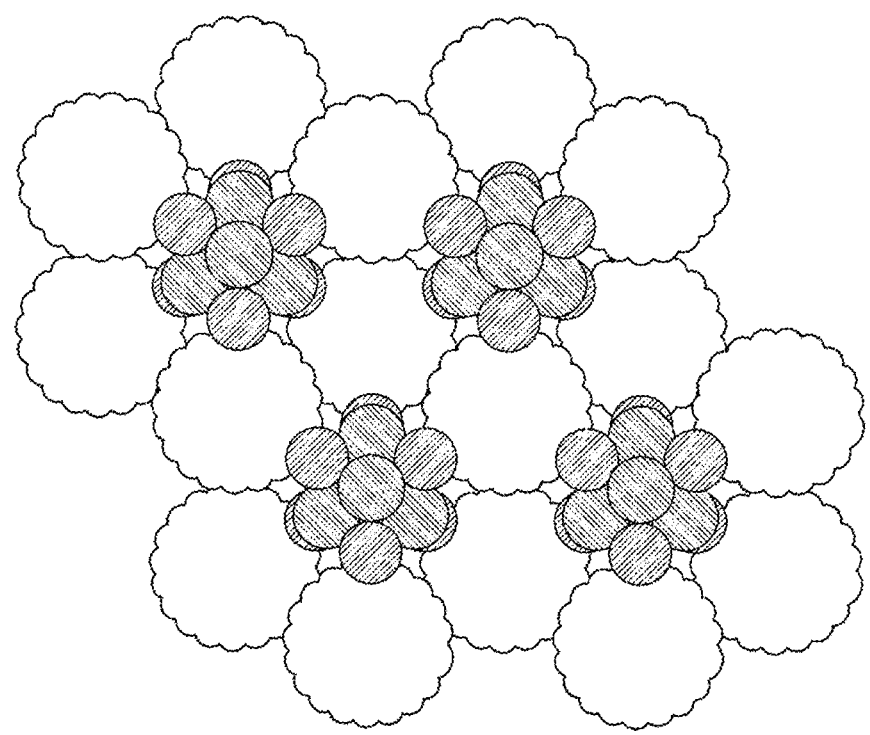
FIG. 3 is a diagram illustrating the space filling molecular structure of $Cr_6Te_8(PEt_3)_6.2C_{60}$ showing the crystal packing looking down the c-axis.
Figure 4:
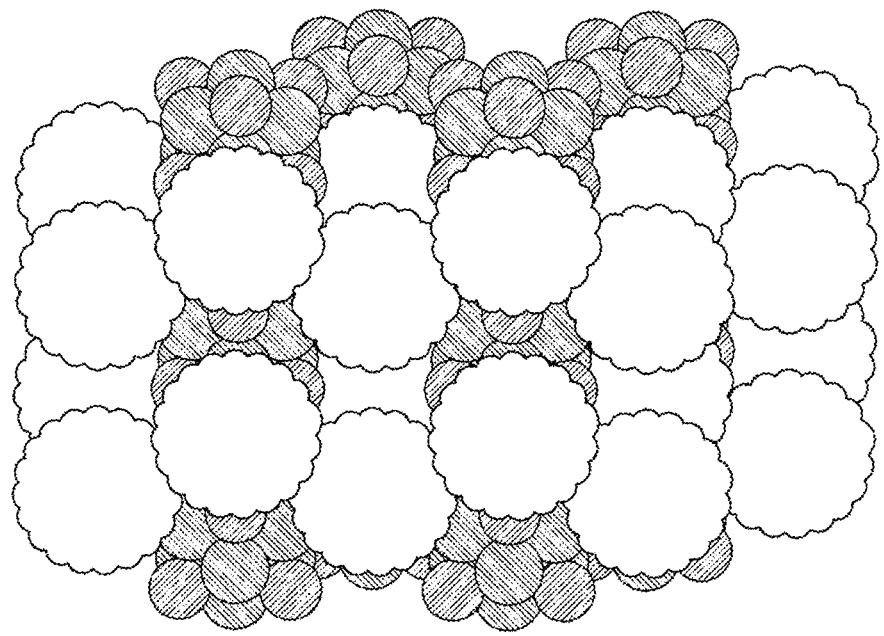
FIG. 4 is a diagram illustrating the space filling molecular structure of $Cr_6Te_8(PEt_3)_6.2C_{60}$ showing the crystal packing looking down the ab-plane.

In accordance with one aspect of the disclosed subject matter, cluster $Cr_6Te_8(PEt_3)_6$ can be combined with two equivalents of $C_{60}$ in toluene and the resulting structure is similar to that of $Co_6Se_8(PEt_3)_6 \cdot 2C_{60}$ described above. For the purpose of illustration and not limitation, FIGS. 3 and 4 show the space filling molecular structure of $Cr_6Te_8(PEt_3)_6 \cdot 2C_{60}$ showing the crystal packing looking down the c-axis (for FIG. 3) and the ab-plane (for FIG. 4). In an exemplary embodiment, the centroid-to-centroid distance between two adjacent $C_{60}$'s can be about 10.3 Å, and/or the $C_{60}$ layers can be about 12.3 Å apart. In FIGS. 3 and 4, carbon is black, phosphorus is orange, and tellurium is teal. The ethyl groups on the phosphines were removed to clarify the view.

Figure 5:
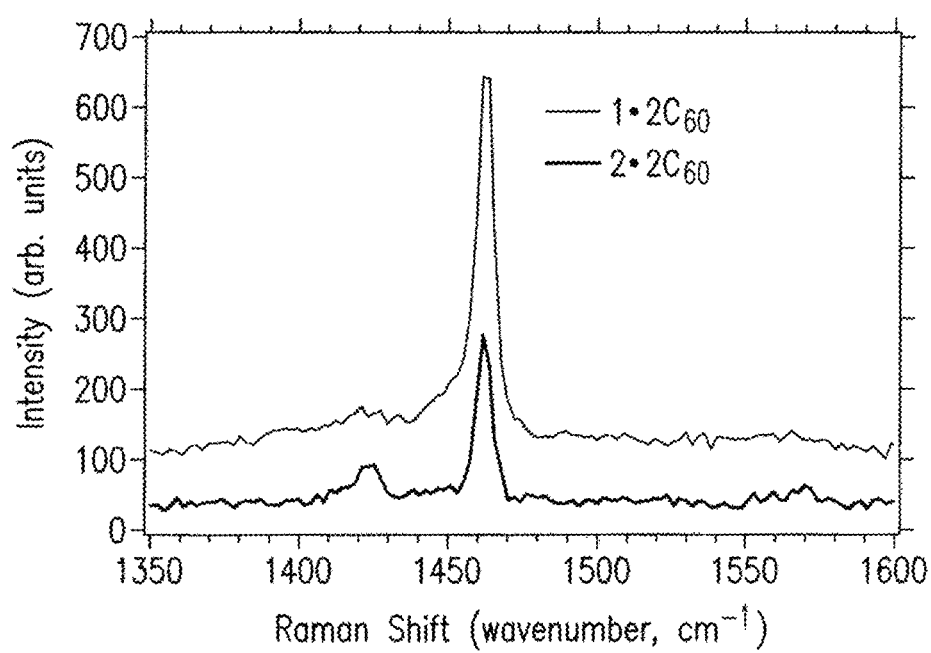
FIG. 5 is a graph of the solid-state Raman spectra of $Co_6Se_8(PEt_3)_6.2C_{60}$ and $Cr_6Te_8(PEt_3)_6.2C_{60}$.

In accordance with one aspect of the disclosed subject matter, using Raman spectroscopy, the amount of charge that is transferred between the components in the solid-state material can be measured. The $A_{2g}$ pentagonal pinch mode of $C_{60}$ (i.e., 1468 cm$^{-1}$ for pristine $C_{60}$) shifts to lower energy by 6 cm$^{-1}$ per electron transferred to $C_{60}$ independent of the dopant or the crystal structure. For the purpose of illustration and not limitation, FIG. 5 shows the solid-state Raman spectra of $Co_6Se_8(PEt_3)_6 \cdot 2C_{60}$ and $Cr_6Te_8(PEt_3)_6 \cdot 2C_{60}$, which were taken using a 514.5 nm excitation laser at 4.6-7.8 kW/cm$^2$ power densities, with the sample loaded in a quartz cuvette sealed under an atmosphere of Ar. The $Co_6Se_8(PEt_3)_6 \cdot 2C_{60}$ spectrum was taken with 78 μW and averaged for 1 hour (i.e., 7.8 kW/cm$^2$ power density). The $Cr_6Te_8(PEt_3)_6.2C_{60}$ spectrum was taken with 46 μW and averaged for 15 minutes (i.e., 4.6 kW/cm$^2$ power density). The $A_{2g}$ pentagonal pinch mode of $C_{60}$ is centered at 1463 cm$^{-1}$ and 1462 cm$^{-1}$ in $Co_6Se_8(PEt_3)_6.2C_{60}$ and $Cr_6Te_8$ (PEt$_3$)$_6$.2C$_{60}$, respectively. The peak position error is ±1 cm$^{-1}$, reflecting the peak position of spectra taken with different samples on different days, and is within experimental error. Therefore, it can be surmised that $Co_6Se_8$(PEt$_3$)$_6$ clusters and $Cr_6Te_8(PEt_3)_6$ clusters transfer two electrons, and each $C_{60}$ receives one electron. The spectra are offset for clarity.

For the Raman measurements, an Ar-Ion laser generates 514.5 nm light. The light enters an inverted microscope where a 40×/0.6 N.A. objective focuses it to a 1 μm$^2$ spot size on the sample, which is inside a sealed, 1 cm thick cuvette. Scattered light is focused through a 50 μm pinhole, recollimated, and refocused into a 0.27 m monochromator, where the light strikes a CCD array detector with 4 cm$^{-1}$ resolution. Typical 514.5 nm powers range from 10 to 80 μW, and collection times range from 15 minutes to 1 hour. Consecutive scans can be performed on the same spot, and scans at 10 μW can be performed to ensure there is no sample degradation or photoproduct buildup. At relatively low power densities (less than 100 W/cm$^2$) pure $C_{60}$ can produce oligomers with the $A_{2g}$ pentagonal pinch mode at 1459 cm$^{-1}$. The absence of a peak at this energy shows that this photoproduct is not generated even at much higher power densities. Control spectra taken with the cluster only produced no signal.

Figure 6:
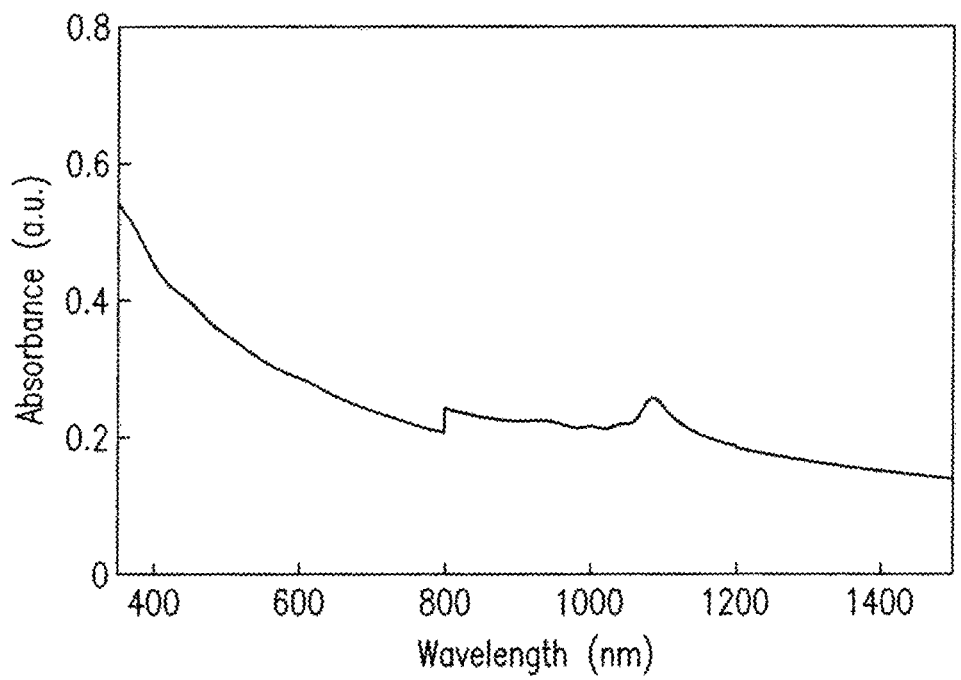
FIG. 6 is a graph of the solid-state electronic absorption spectrum of $Co_6Se_8(PEt_3)_6.2C_{60}$ dispersed in KBr.
Figure 7:
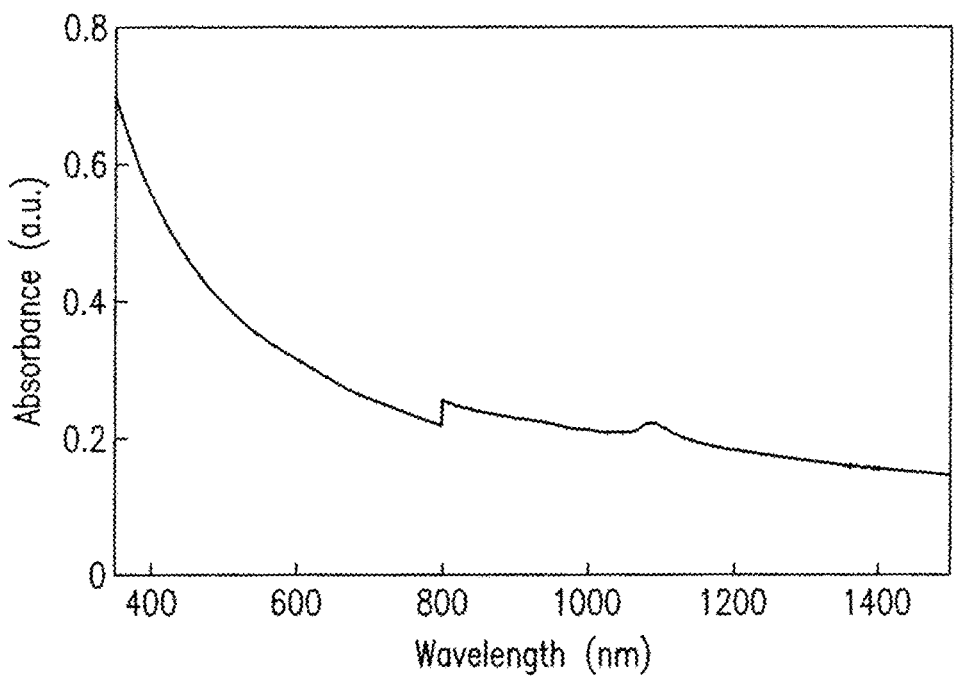
FIG. 7 is a graph of the solid-state electronic absorption spectrum of $Cr_6Te_8(PEt_3)_6.2C_{60}$ dispersed in KBr.

In accordance with one aspect of the disclosed subject matter, the solid-state electronic absorption spectra of $Co_6Se_8(PEt_3)_6.2C_{60}$ and $Cr_6Te_8(PEt_3)_6.2C_{60}$ provide additional confirmation for the formation of charge transfer complexes in the materials. For the purpose of illustration and not limitation, FIGS. 6 and 7 are graphs of the solid-state electronic absorption spectrum of $Co_6Se_8(PEt_3)_6.2C_{60}$ and $Cr_6Te_8(PEt_3)_6.2C_{60}$, respectively, dispersed in KBr. The electronic absorption spectra were taken on an Agilent Technologies Cary 5000 UV-vis-NIR spectrophotometer. The sample was ground with KBr and pressed into a pellet. A background spectrum collected using a pristine KBr pellet was subtracted. As illustrated in FIGS. 6 and 7, the electronic spectra of both materials dispersed in KBr pellets show a series of transitions in the range 900-1150 nm with the strongest band centered at 1100 nm. These features are transitions for the radical anion of fullerene, $C_{60}.^-$. The $Co_6Se_8(PEt_3)_6$ cluster has four transitions in the range 350-700 nm. These weak transitions are observed in $Co_6Se_8$ (PEt$_3$)$_6$.2C$_{60}$ but not in $Cr_6Te_8(PEt_3)_6.2C_{60}$.

In accordance with one aspect of the disclose subject matter, the solid-state compounds described above can be viewed as [cluster$^{2+}$][C$_{60}^-$]$_2$, which can be compared to traditional simple M$^{2+}$X$^{1-}$$_2$ solids, e.g. the CdI$_2$ structure. The CdI$_2$ structure is formed by a hexagonally close-packed array of monoanions with half of the octahedral interstitial sites occupied by dications. The cations are ordered such that along the crystallographic c-direction the cation layers are alternatively empty and fully occupied. This results in a layered material, the layers being held together by van der Waals bonding between anions of neighboring layers.

Figure 8A:
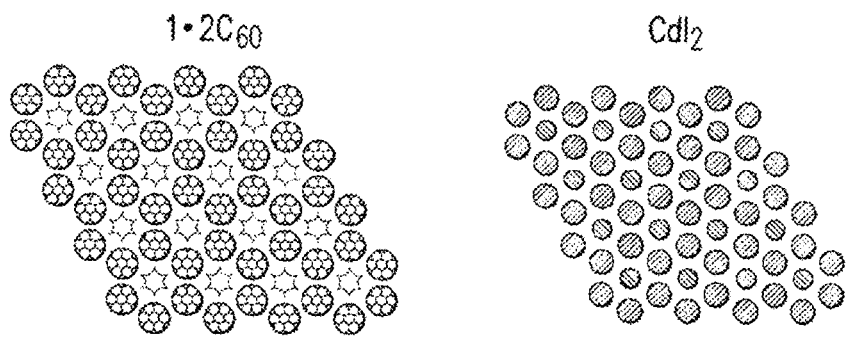
FIGS. 8A, 8B, 8C, and 8D are wireframe-representations of $Co_6Se_8(PEt_3)_6.2C_{60}$ as compared to wireframe-representations of $CdI_2$.
Figure 8B:
Figure 8C:
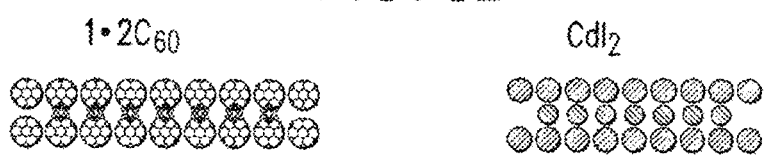
Figure 8D:
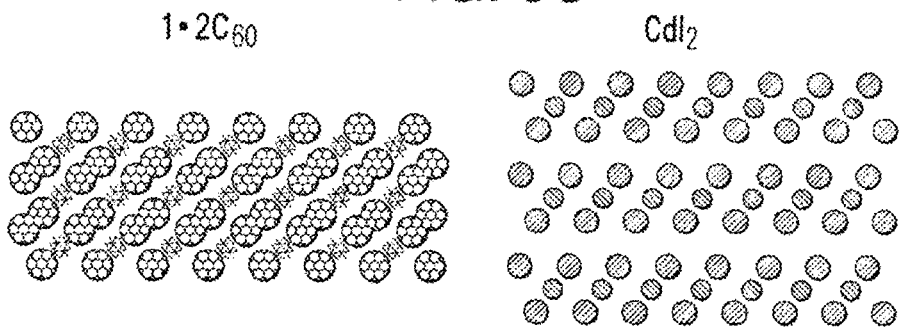

The structures of compounds $Co_6Se_8(PEt_3)_6.2C_{60}$ and $Cr_6Te_8(PEt_3)_6.2C_{60}$ can be appreciated in these same terms, i.e. they can assemble into a superatomic relative of the CdI$_2$ structure type. For the purpose of illustration and not limitation, FIG. 8 displays wireframe-representations of $Co_6Se_8$(PEt$_3$)$_6$.2C$_{60}$ and shows a comparison of the packing structures of $Co_6Se_8(PEt_3)_6.2C_{60}$ and CdI$_2$. The $Co_6Se_8(PEt_3)_6$ cluster and Cd are shown in blue and $C_{60}$ and I are shown in grey. The ethyl groups on the phosphines were removed to clarify the view. In FIG. 8A one $C_{60}$-cluster-$C_{60}$ hexagonal layer is shown looking down the c-axis, comparing it to the corresponding layer in CdI$_2$. FIGS. 8B and 8C show edge-on views of the same layer looking down the ab-plane. FIG. 8D shows stacking of the ab hexagonal layers along the c-axis direction. The similarity between the structures of the compounds $Co_6Se_8(PEt_3)_6.2C_{60}$ and $Cr_6Te_8(PEt_3)_6.2C_{60}$ and the 'atomic' solid, i.e., in CdI$_2$, is evident in FIGS. 8A, 8B, 8C, and 8D. While the atomic solid CdI$_2$ appears in many different polytypes, which are related by different patterns of stacking of ab planes, only one stacking polytype has been observed for cluster solids $Co_6Se_8(PEt_3)_6.2C_{60}$ and $Cr_6Te_8(PEt_3)_6.2C_{60}$.

Figure 9A:
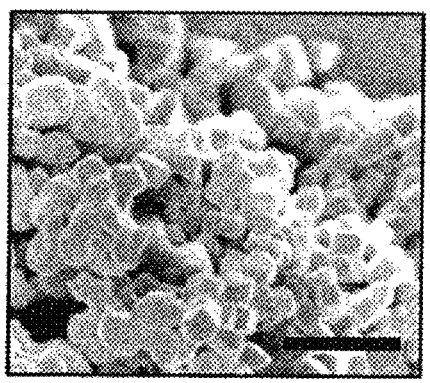
FIG. 9A is a scanning electron micrograph of $Ni_9Te_6(PEt_3)_8.C_{60}$.

In accordance with another aspect of the disclosed subject matter, cluster $Ni_9Te_6(PEt_3)_8$ reacts quickly with $C_{60}$ in toluene to give a dark brown precipitate that is composed of nanometer-sized cubic crystals, which can be seen in FIG. 9A showing a scanning electron micrograph of $Ni_9Te_6(PEt_3)_8.C_{60}$, with a scale bar of 1 μm for the purpose of illustration and not limitation. The micrographic image was taken on a high-resolution field emission scanning electron microscope (i.e., Hitachi S-4700), with the sample deposited directly on carbon tape.

Figure 10:
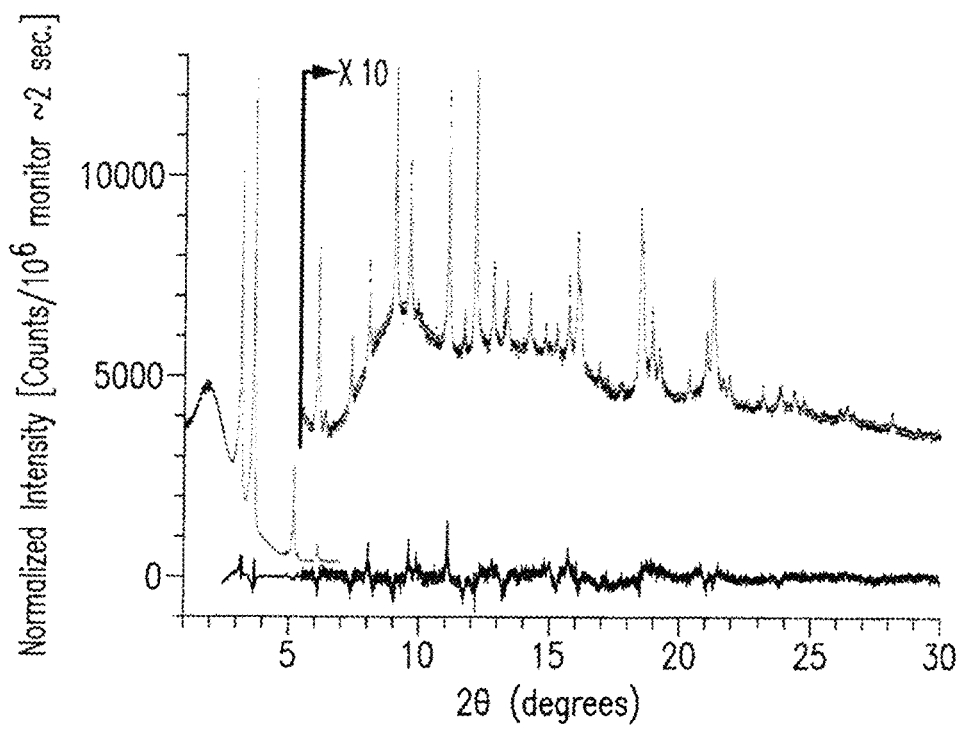
FIG. 10 is a graph of the Rietveld refinement of $Ni_9Te_6(PEt_3)_8.C_{60}$.

Rietveld refinement of the synchrotron powder X-ray diffraction data, as shown in FIG. 10 for the purpose of illustration and not limitation, indicates that this solid is a 1:1 combination of $Ni_9Te_6(PEt_3)_8$ and $C_{60}(3.C_{60})$. In the figure, black dots are data, the red trace is the fit, and the lower black trace is the difference, to the same scale. The vertical scale is expanded by a factor of 10 above 5.5°.

Figure 9B:
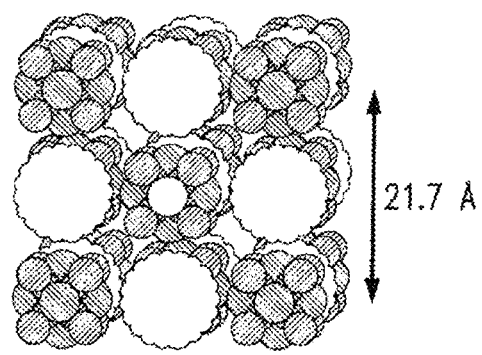
FIG. 9B is a diagram illustrating the space filling molecular structure of $Ni_9Te_6(PEt_3)_8.C_{60}$.

For the purpose of illustration and not limitation, FIG. 9B shows the space filling molecular structure of $Ni_9Te_6$ (PEt$_3$)$_8$.C$_{60}$. In the figure, carbon is black, nickel is red, phosphorus is orange, and tellurium is teal. The ethyl groups on the phosphines were removed to clarify the view. The face centered cubic structure can have a lattice parameter of 21.7 Å and is analogous to the rock-salt crystal. In this material, the constituent clusters are able to communicate together to produce a magnetically ordered phase at low temperature, akin to atoms in a solid-state compound.

Figure 11:
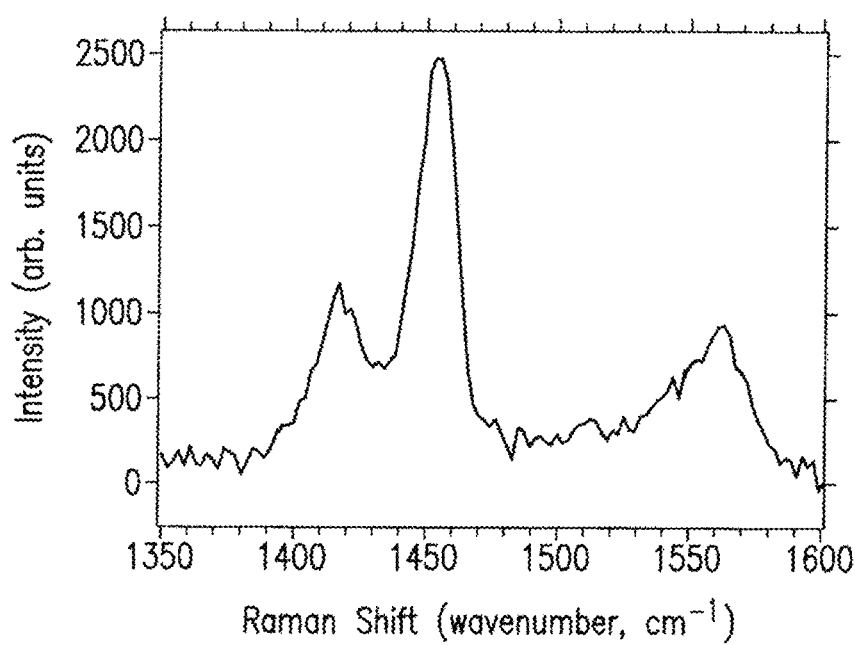
FIG. 11 is a graph of the Raman spectrum of $Ni_9Te_6(PEt_3)_8.C_{60}$.

In accordance with one aspect of the disclosed subject matter, because the cluster $Ni_9Te_6(PEt_3)_8$ is rich in metal, it is expected to have a greater reducing power than $Co_6Se_8$(PEt$_3$)$_6$ or $Cr_6Te_8(PEt_3)_6$. For the purpose of illustration and not limitation FIG. 11 shows Raman spectrum of $Ni_9Te_6$(PEt$_3$)$_8$.C$_{60}$. The spectrum was taken with 30 μW laser power averaged for 1 hour (3.0 kW/cm$^2$ power density). The broad main peak is centered at 1454±3 cm$^{-1}$, with the error reflecting the peak position of different samples on different days. This peak cannot be unambiguously assigned to the $A_{2g}$ mode of $C_{60}$, but the data suggests that the fullerene in $Ni_9Te_6(PEt_3)_8.C_{60}$ is more reduced than in $Co_6Se_8$(PEt$_3$)$_6$.2C$_{60}$ or $Cr_6Te_8(PEt_3)_6.2C_{60}$. According, binary cluster materials can be prepared with diverse structural and ionic properties by changing the composition of the molecular cluster building block.

Solid-state materials in accordance with the disclosed subject matter can behave less like molecular co-crystals and more like three-dimensional solid-state compounds. For example, the materials exhibit activated electronic transport. For the purpose of illustration and not limitation, FIG. 12A displays the electrical transport properties, i.e. a plot of the conductance vs. 1/T, for $Co_6Se_8(PEt_3)_6.2C_{60}$ and FIG. 13 shows the transport properties of $Cr_6Te_8(PEt_3)_6.2C_{60}$. For FIG. 12A, four probes conductance measurements were performed on a single crystal (shown in black) and a pressed pellet (shown in red) and the Arrhenius fits are shown as solid lines. For FIG. 13, two probes conductance measurements were performed on a pressed pellet. For the purpose of illustration and not limitation, FIG. 14 shows an optical micrograph of a single crystal device used to measure the electrical transport properties of $Co_6Se_8(PEt_3)_6 \cdot 2C_{60}$ with a scale bar of 100 μm. Single crystals of $Co_6Se_8(PEt_3)_6 \cdot 2C_{60}$ were grown directly onto a prefabricated device assembled on a Si substrate with a 300 nm $SiO_2$ layer. Prior to the crystal growth, Au electrodes separated by a 10 μm gap were deposited on the substrate by evaporating the metal through a shadow mask. Compounds $Co_6Se_8(PEt_3)_6 \cdot 2C_{60}$ and $Cr_6Te_8(PEt_3)_6 \cdot 2C_{60} \cdot 2C_{60}$ were also sintered into pellets. The material was loaded into a 6 mm vacuum pellet die and pressed under a load of 4 tons. Electrical contact was made with silver paste. The electrical transport measurements of $Co_6Se_8(PEt_3)_6 \cdot 2C_{60}$ and $Cr_6Te_8(PEt_3)_6 \cdot 2C_{60} \cdot 2C_{60}$ were performed using a continuous flow cryostat system (available from Janis Research Company Inc.). The electrical conductance in both two probes and four probes configurations was measured using a source meter (i.e., Yokogawa GS200 DC voltage/current source) and an electrometer (i.e., Keithley 6514 programmable electrometer).

Figure 12A:
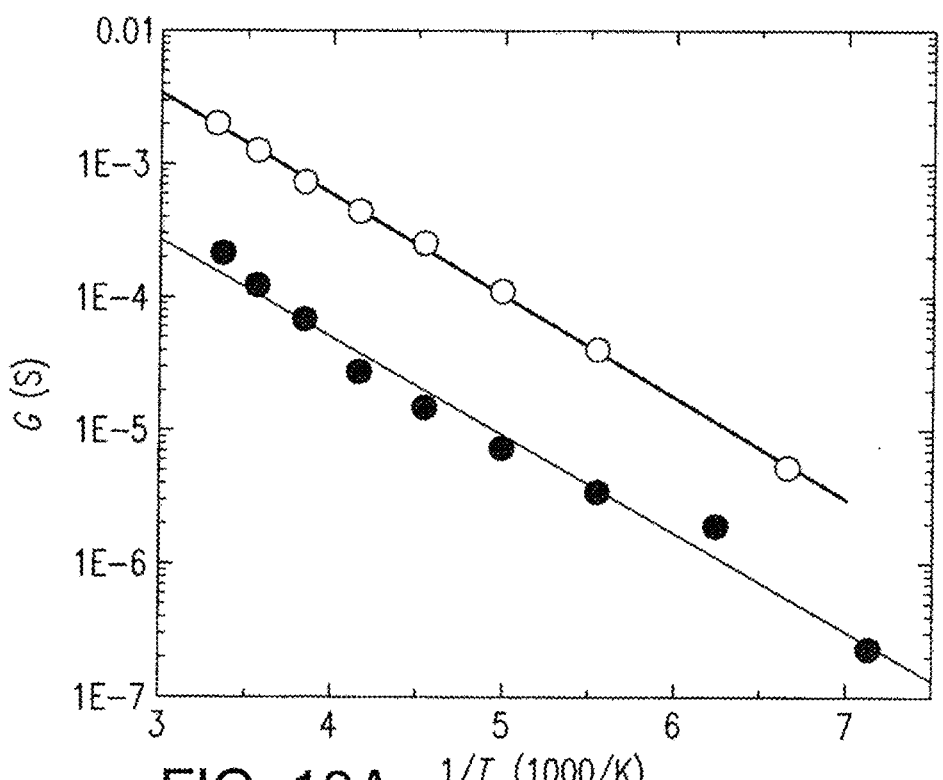
FIG. 12A is a graph of the conductance vs. 1/T, for $Co_6Se_8(PEt_3)_6 \cdot 2C_{60}$.
Figure 13:
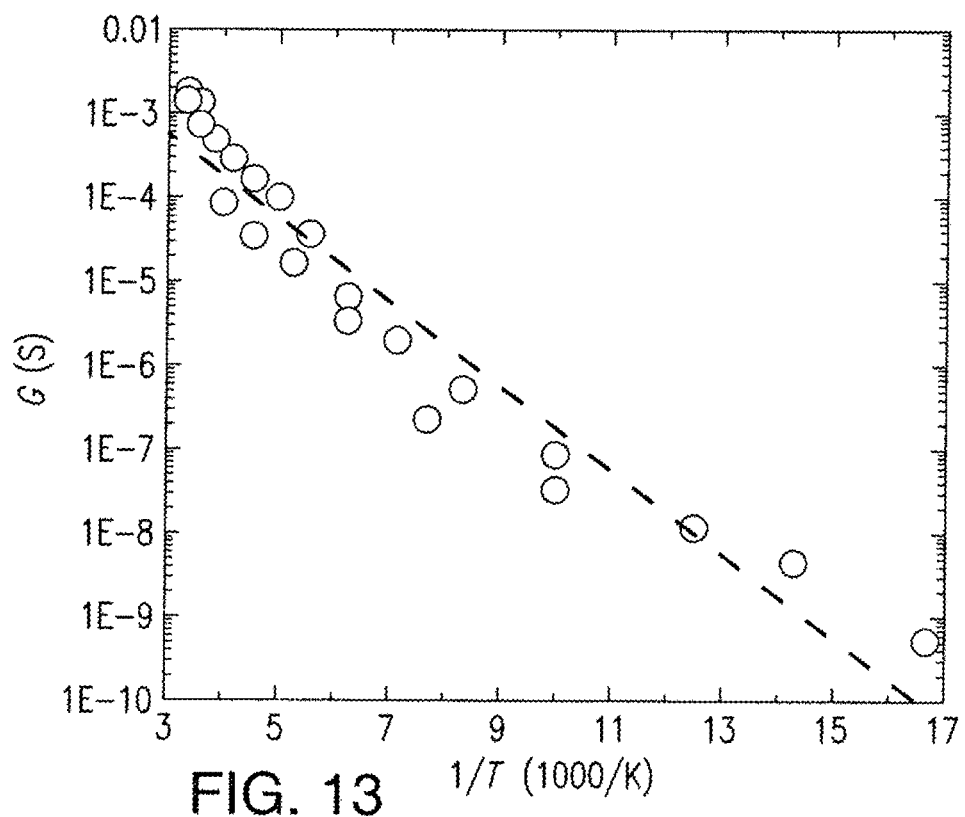
FIG. 13 is a graph of conductance vs. 1/T for $Cr_6Te_8(PEt_3)_6 \cdot 2C_{60}$.
Figure 14:
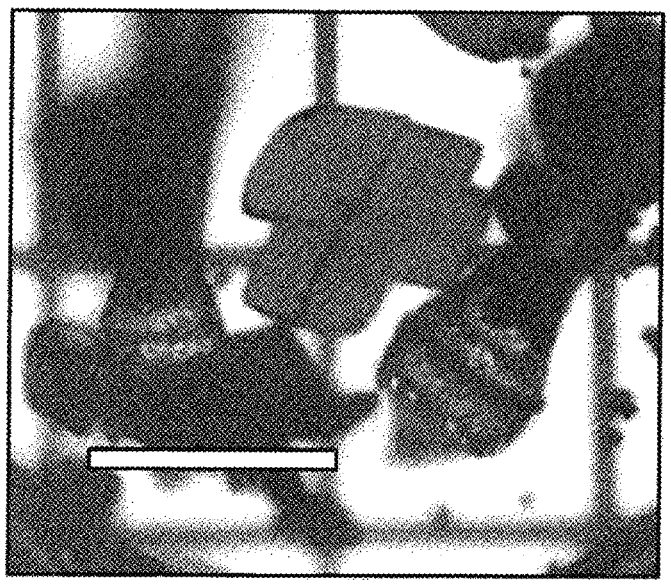
FIG. 14 is an optical micrograph of a single crystal device used to measure the electrical transport properties of $Co_6Se_8(PEt_3)_6 \cdot 2C_{60}$ with a scale bar of 100 μm.

As demonstrated by FIGS. 12A and 13, both compounds can be good electrical conductors with resistivities on the order of 10 Ωcm at room temperature. An exponential decrease of the conductance (G) is observed with decreasing temperature. This thermally activated semiconducting behavior can be modeled using the equation:

$$G = G_0 e^{-E_a/kT} \quad (1)$$

where $G_0$ is the pre-exponential factor, $E_a$ is the activation energy for charge transfer and k is the Boltzmann constant. No significant difference between the measurements done on single crystals or on pressed pellets using two or four terminals is observed. Thermal activation energies of ~150 meV and ~100 meV for $Co_6Se_8(PEt_3)_6 \cdot 2C_{60}$ and $Cr_6Te_8(PEt_3)_6 \cdot 2C_{60}$, respectively can be calculated from the slope of the Arrhenius plots, as known to one of ordinary skill in the art. This data indicates that $Co_6Se_8(PEt_3)_6 \cdot 2C_{60}$ and $Cr_6Te_8(PEt_3)_6 \cdot 2C_{60}$ are both gapped semiconductors and show activated electronic transport with activation energies of 100-150 meV.

Figure 12B:
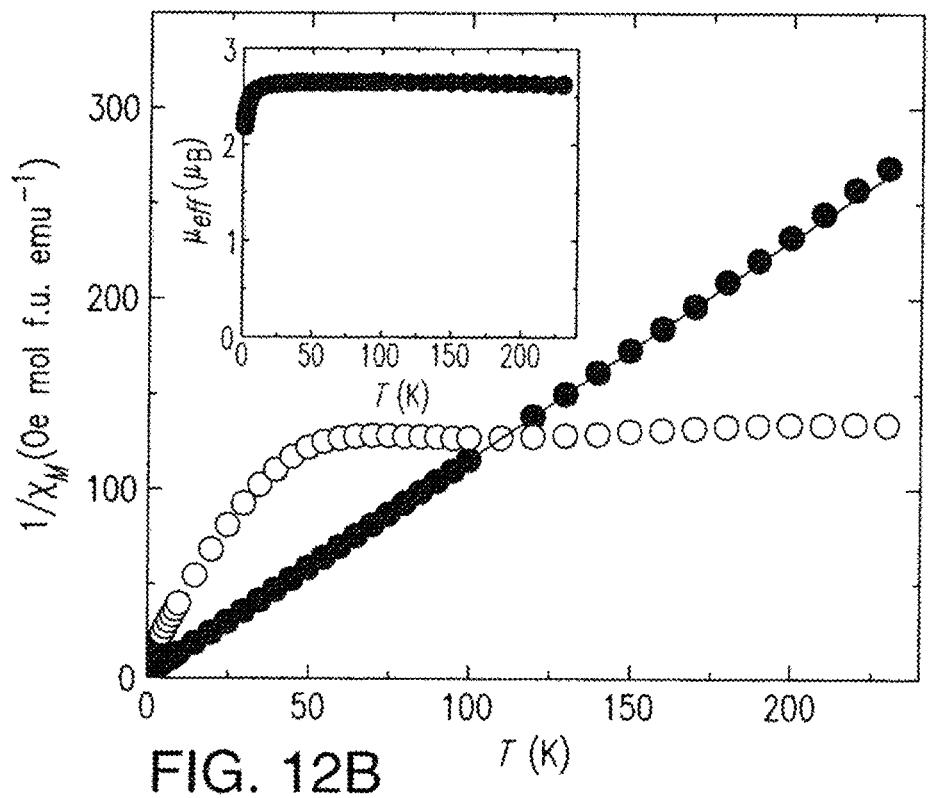
FIG. 12B is a graph of the inverse magnetic susceptibility as a function of temperature for $Co_6Se_8(PEt_3)_6 \cdot 2C_{60}$ (circles) and $Cr_6Te_8(PEt_3)_6 \cdot 2C_{60}$ (open circles).

An additional feature of these superatom-assembled solids is that the magnetic properties vary as the inorganic cores are changed due to the vastly different spin states accessible with the molecular clusters. For the purpose of illustration and not limitation, FIG. 12B shows the temperature dependence of the inverse molar magnetic susceptibility ($1/\chi_M$) (black) and the effective magnetic moment ($\mu_{eff}$) of $Co_6Se_8(PEt_3)_6 \cdot 2C_{60}$ (filled circles) from SQUID magnetometry in an applied external field H=1 T. The magnetic data was collected on a Quantum Design SQUID magnetometer. The sample was encapsulated in a gel capsule under an atmosphere of Ar. The capsule was mounted using a clear plastic straw. The data was corrected for diamagnetic and temperature independent contributions and was modeled using a modified Curie-Weiss law:

$$\chi_M(T) = C/(T-\Theta) + \chi_D + \chi_{TIP}, \quad (2)$$

where C is the Curie constant, Θ is the Weiss constant, and $\chi_D$ and $\chi_{TIP}$ are the diamagnetic and temperature independent paramagnetic contributions, respectively. A good fit (shown in red) is obtained with C=0.9 emu K Oe$^{-1}$ mol f.u.$^{-1}$ (f.u.=formula unit), Θ=−0.3 K and $\chi_{TIP}$=0.001 emu Oe$^{-1}$ mol$^{-1}$. The small negative Weiss constant indicates weak antiferromagnetic interactions. Above 10 K, $Co_6Se_8(PEt_3)_6 \cdot 2C_{60}$ shows a temperature independent effective magnetic moment, $\mu_{eff}$=2.7 $\mu_B$ per f.u. This agrees well with the spin-only value of 2.8 $\mu_B$ for two non-interacting unpaired electrons and is consistent with the Raman spectroscopy data that show one electron in each of the two $C_{60}$s per formula unit, with the cobalt ions in the cluster not contributing to the overall moment. The effective magnetic moment of $Co_6Se_8(PEt_3)_6 \cdot 2C_{60}$ as a function of temperature is shown in the inset.

FIG. 12B also displays the temperature dependence of the inverse molar magnetic susceptibility ($1/\chi_M$) (black) of $Cr_6Te_8(PEt_3)_6 \cdot 2C_{60}$ (open circles). The important result is that this assembly $Cr_6Te_8(PEt_3)_6 \cdot 2C_{60}$ exhibits a complex magnetic behavior that doesn't fit a simple Curie-Weiss law. An obvious change in the slope of this plot around 60 K is observed. The difference in the materials can be due to the large magnetic difference between compound ($Co_6Se_8(PEt_3)_6$)$^{2+}$, which contains six Co$^{III}$, and compound ($Cr_6Te_8(PEt_3)_6$)$^{2+}$, which is composed of six Cr$^{III}$.

Figure 12C:
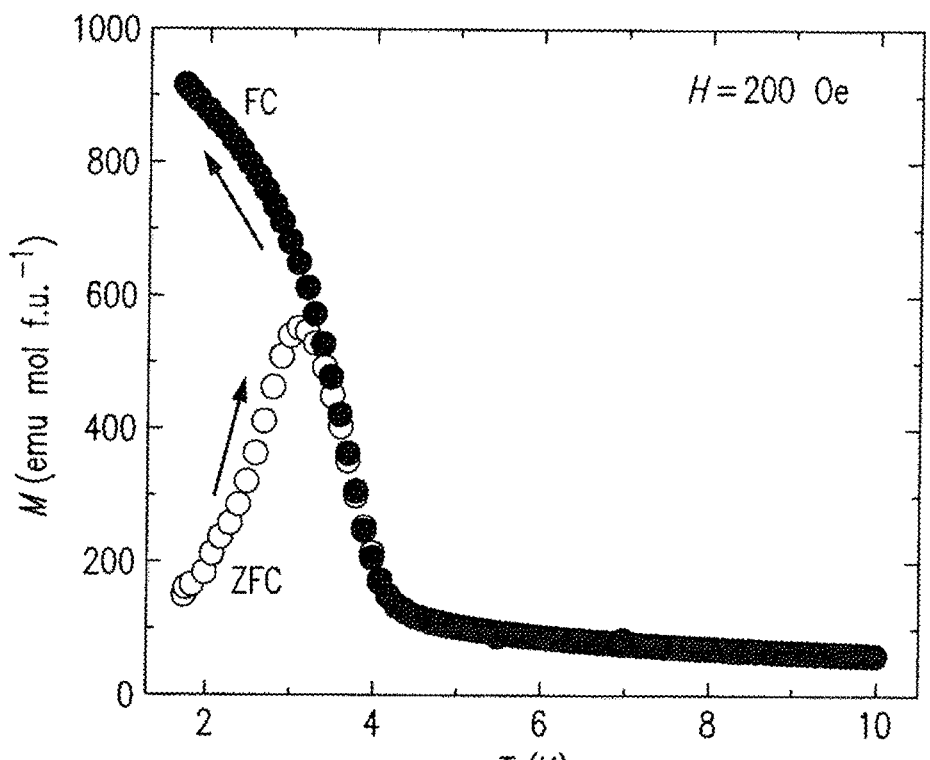
FIG. 12C is a graph of the temperature dependence of the ZFC and FC magnetization of $Ni_9Te_6(PEt_3)_8 \cdot C_{60}$ in an applied external field H=200 Oe.

In accordance with one aspect of the disclosed subject matter, the magnetism of the rock-salt $Ni_9Te_6(PEt_3)_8 \cdot C_{60}$ material is different from that of $Co_6Se_8(PEt_3)_6 \cdot 2C_{60}$ and $Cr_6Te_8(PEt_3)_6 \cdot 2C_{60}$ both in magnitude and as a function of temperature. For the purpose of illustration and not limitation, FIG. 12C shows the temperature dependence of the ZFC and FC magnetization (M) of $Ni_9Te_6(PEt_3)_8 \cdot C_{60}$ in an applied external field H=200 Oe. In the ZFC experiment, the sample was cooled down from room temperature to 1.8 K in zero-field prior to the measurement of M from 1.8 K to 10 K. A transition to a magnetically ordered phase below ~4.4 K is observed. The irreversibility indicated by the difference between the zero-field cooled (ZFC) and field-cooled (FC) magnetizations is consistent with a spin glass transition. This suggests that the constituent clusters can communicate magnetically at low temperature, akin to atoms in a solid-state compound.

Example 1—Compound $Co_6Se_8(PEt_3)_6 \cdot 2C_{60}$

Cluster $Co_6Se_8(PEt_3)_6$ (17.5 mg, 10.3 μmol) was dissolved in 5 mL of toluene and filtered with a 0.2 μm syringe filter. $C_{60}$ (14.8 mg, 20.6 μmol) (available from BuckyUSA) was dissolved in 5 mL of toluene and filtered with a 0.2 μm syringe filter. The two solutions were combined in a vial. Black crystals were obtained overnight. The supernatant was decanted, the solid was washed with toluene and dried under vacuum for ~12 h. The yield was 25.1 mg, or 78%.

Example 2—Compound $Cr_6Te_8(PEt_3)_6 \cdot 2C_{60}$

Cluster $Cr_6Te_8(PEt_3)_6$ (21.0 mg, 10.3 μmol) was dissolved in 5 mL of toluene and filtered with a 0.2 μm syringe filter. $C_{60}$ (14.8 mg, 20.6 μmol) was dissolved in 5 mL of toluene and filtered with a 0.2 μm syringe filter. The two solutions were combined in a vial. Black crystals were obtained overnight. The solid was centrifuged, rinsed with toluene and dried under vacuum for ~12 h. The yield was 29.5 mg, or 82%.

Example 3—Compound $Ni_9Te_6(PEt_3)_8 \cdot C_{60}$ $C_{60}$ (18.9 mg, 8.4 μmol) was dissolved in 5 mL of toluene and filtered with a 0.2 μm syringe filter into a vial. Cluster $Ni_9Te_6(PEt_3)_8$ (6.1 mg, 8.5 μmol) was dissolved in 5 mL of toluene, filtered with a 0.2 μm syringe filter and added drop-wise to the stirred $C_{60}$ solution. A dark brown precipitate formed instantly. The slurry was stirred for 5 min. The solid was centrifuged, rinsed with toluene and dried under vacuum for ~12 h. The yield was 24 mg, or 96%.

Example 4—X-Ray Diffraction

The single crystal X-ray diffraction data of $Co_6Se_8(PEt_3)_6.2C_{60}$ described above was collected using an Oxford Diffraction Xcalibur-2 CCD diffractometer with graphite monochromatized $MoK_\alpha$ radiation. The crystal was mounted in a cryoloop under Paratone-N oil and cooled to 100K with an Oxford Diffraction Cryojet system. The collected frames were analyzed using the Crysalis program package, and integrated intensities were corrected for absorption using the Gaussian integration method.

The single crystal X-ray diffraction data of $Cr_6Te_8(PEt_3)_6.2C_{60}$ described above was collected on a Bruker SMART CCD APEX II diffractometer with graphite monochromated $CuK_\alpha$ radiation. The crystal was mounted in a Cryoloop using Paratone-N oil and cooled to 100K with an Oxford Cryosystems 700 Series Cryostream Plus unit. Data were collected and integrated using the Bruker SAINT software package, and integrated intensities were corrected for absorption using a multi-scan technique (SADABS).

High resolution powder X-ray diffraction (PXRD) measurements of $Ni_9Te_6(PEt_3)_8.C_{60}$ were collected on the X16C beam line at the National Synchrotron Light Source, Brookhaven National Laboratory. A Si(111) channel-cut monochromator selected a parallel 0.6997 Å incident beam. The diffracted X-rays were analyzed by a Ge(111) crystal and detected using a NaI scintillation counter. The powder was sealed in a glass capillary of 1 mm nominal diameter, which was spun at several Hz during data collection to improve particle statistics. Data were collected over a 2θ range 1° to 30°, in increments of 0.005°, with count time increasing from 10 to 30 sec per point over that range.

The single crystal data of $Co_6Se_8(PEt_3)_6.2C_{60}$ and $Cr_6Te_8(PEt_3)_6.2C_{60}$ were first analyzed with the NRCVAX program package. For all subsequent calculations and refinements, the program CRYSTALS was used. The merohedral twinning in space group P$\bar{3}$ was addressed by introducing twin conditions, with the two possible twin volumes refining to values close to 0.5. Data for $Co_6Se_8(PEt_3)_6.2C_{60}$ allowed full refinement of all individual atoms in the structure, whereas for $C_6Te_8(PEt_3)_6.2C_{60}$, the data quality did not allow an unconstrained refinement. There, restraints were introduced to keep carbon-carbon bonds in the $C_{60}$ clusters within an acceptable range. Furthermore, anisotropic refinements of the carbon atoms in the $C_{60}$ clusters indicated sizeable rotational motion of the $C_{60}$ cluster, even at 100K, leading to non-elliptical atomic displacement parameters. Where feasible, hydrogen atoms were placed geometrically and constrained to the connecting carbon atom. For $Cr_6Te_8(PEt_3)_6.2C_{60}$, only the main cluster atoms, Cr, Te, and P could be refined anisotropically, whereas all other atoms were refined with isotropic displacement parameters.

Visual inspection of the powder X-ray diffraction pattern of $Ni_9Te_6(PEt_3)_8.C_{60}$ suggested an fcc structure, subsequently confirmed by Rietveld refinement using TOPAS-Academic software. The structure was refined from models based on the published literature. The Rietveld fit (FIG. 10) cannot distinguish the orientation of the fullerene; for the purpose of illustration, it was placed with two-fold axes along the lattice translations, but it can well be orientationally disordered. The large background and broad peak centered at 2θ≈2° (d~20 Å) in the powder diffraction pattern suggest the presence of a significant amount of disordered material, likely composed of $Ni_9Te_6(PEt_3)_8$ and $C_{60}$.

Example 5—Selected Crystallographic Data

For the purpose of illustration and not limitation, Table 1 summarizes selected crystallographic data obtain by the method and examples described herein for the exemplary solid-state compounds in accordance with the disclosed subject matter.

TABLE 1

| Compound | 1•$2C_{60}$ | 2•$2C_{60}$ | 3•$C_{60}$ |
|---|---|---|---|
| Formula | $C_{156}H_{90}Co_6P_6Se_8$ | $C_{156}H_{90}Cr_6P_6Te_8$ | $C_{108}H_{120}Ni_9P_8Te_6$ |
| MW | 3135.55 | 3483.05 | 2959.74 |
| Lattice type | Trigonal | Trigonal | Cubic |
| Space group | P$\bar{3}$ | P$\bar{3}$ | Fm$\bar{3}$ |
| a (Å) | 15.7500(8) | 16.1818(3) | 21.6808(8) |
| b (Å) | 15.7500(8) | 16.1818(3) | 21.6808(8) |
| c (Å) | 12.4792(4) | 12.3581(6) | 21.6808(8) |
| α (°) | 90 | 90 | 90 |
| β (°) | 90 | 90 | 90 |
| γ (°) | 120 | 120 | 90 |
| V (Å$^3$) | 2680.9(2) | 2802.44(15) | 10191(1) |
| Z value | 1 | 1 | 4 |
| $D_{calc}$ (g cm$^{-3}$) | 1.94 | 2.06 | 1.93 |
| T (K) | 100 | 100 | 295 |
| GOF on F$^2$ | 0.9723 | 1.0757 | |
| $R_1{}^a$[F$^2$ > 2σ (F$^2$)] | 0.0600 | 0.0932 | |
| $wR_2{}^b$ (all data) | 0.1419 | 0.2329 | |
| $R_{WP}{}^c$ | | | 0.0319 |
| $\chi^{2d}$ | | | 6.00 |

$$^aR_1 = \frac{\sum \||F_o|-|F_c|\|}{\sum |F_o|};$$

$$^bwR_2 = \left[\frac{\sum w(F_o^2-F_c^2)^2}{\sum w(F_o^2)^2}\right]^{1/2};$$

$$^cR_{WP} = \left[\frac{\sum (y_{2\theta}^{obs}-y_{2\theta}^{calc})^2/\sigma_{2\theta}^2}{\sum (y_{2\theta}^{obs})^2/\sigma_{2\theta}^2}\right]^{1/2};$$

$$^d\chi^2 = \frac{\sum (y_{2\theta}^{obs}-y_{2\theta}^{calc})^2/\sigma_{2\theta}^2}{N-P}$$

The foregoing merely illustrates the principles of the disclosed subject matter. Various modifications and alterations to the described embodiments will be apparent to those skilled in the art in view of the teachings herein. For example, various values and ranges, including dimensions, properties, and times, are provided in the descriptions of the exemplary embodiments, and a person skilled in the art will be able to modify the values and ranges for use in particular applications within the scope of the disclosed subject matter. It will be appreciated that those skilled in the art will be able to devise numerous modifications which, although not explicitly described herein, embody its principles and are thus within its spirit and scope.

The invention claimed is:

1. A solid-state material comprising a solid-state compound having the formula:

[Cluster1][Cluster2]$_n$ wherein
Cluster1 comprises $Co_6Se_8(PEt_3)_6$;
Cluster2 comprises a carbon cluster;
n is the number of Cluster2 clusters in the solid-state compound and n is greater than or equal to 1; and Cluster1 and Cluster2 are arranged in a binary assembly by charge transfer to form the solid-state material.

2. The solid-state material of claim 1, wherein the Cluster2 comprises $C_{60}$ and n is 2.

3. The solid-state material of claim 2, wherein the solid-state material is assembled into a superatomic relative of a $CdI_2$ structure.

4. The solid-state material of claim 2, wherein the solid-state material comprises hexagonal arrays of $C_{60}$ in a chair-like arrangement that is separated by layers of the $Co_6Se_8(PEt_3)_6$ clusters.

5. The solid-state material of claim 2, wherein the solid-state material includes at least two $C_{60}$ layers spaced apart by about 12.5 Å.

6. The solid-state material of claim 2, wherein the solid-state material includes at least two $C_{60}$s having a centroid-to-centroid distance about 9.9 Å and a shortest non-bonded C—C spacing of about 3.4 Å.

7. The solid-state material of claim 2, wherein each $Co_6Se_8(PEt_3)_6$ cluster transfers two electrons and each $C_{60}$ cluster receives one electron.

8. The solid-state material of claim 2, wherein the solid state material has a thermal activation energy of about 150 meV.

9. The solid-state material of claim 1, wherein the solid-state material is used in an electronic material.

10. The solid-state material of claim 1, wherein the solid-state material is used in a flexible electronic material.

11. A solid-state material comprising a solid-state compound having the formula:

[Cluster1][Cluster2]$_n$, wherein
Cluster1 comprises $Cr_6Te_8(PEt_3)_6$;
Cluster2 comprises a carbon cluster;
n is the number of Cluster2 clusters in the solid-state compound and n is greater than or equal to 1; and
Cluster1 and Cluster2 are arranged in a binary assembly by charge transfer to form the solid-state material.

12. The solid-state material of claim 11, wherein the Cluster2 comprises $C_{60}$ and n is 2.

13. The solid-state material of claim 12, wherein the solid-state material is assembled into a superatomic relative of a $CdI_2$ structure.

14. The solid-state material of claim 12, wherein the solid-state material comprises hexagonal arrays of $C_{60}$ in a chair-like arrangement that is separated by layers of the $Cr_6Te_8(PEt_3)_6$ clusters.

15. The solid-state material of claim 12, wherein the solid-state material includes at least two $C_{60}$ layers spaced apart by about 12.3 Å.

16. The solid-state material of claim 12, wherein the solid-state material includes at least two $C_{60}$s having a centroid-to-centroid distance about 10.3 Å and a shortest non-bonded C—C spacing of about 3.7 Å.

17. The solid-state material of claim 12, wherein each $Cr_6Te_8(PEt_3)_6$ cluster transfers two electrons and each $C_{60}$ cluster receives one electron.

18. The solid-state material of claim 12, wherein the solid state material has a thermal activation energy of about 100 meV.

19. A solid-state material comprising a solid-state compound having the formula:

[Cluster1][Cluster2]$_n$, wherein
Cluster1 comprises $Ni_9Te_6(PEt_3)_8$;
Cluster2 comprises a carbon cluster;
n is the number of Cluster2 clusters in the solid-state compound and n is greater than or equal to 1; and
Cluster1 and Cluster2 are arranged in a binary assembly by charge transfer to form the solid-state material.

20. The solid-state material of claim 19, wherein the Cluster2 comprises $C_{60}$ and n is 1.

21. The solid-state material of claim 19, wherein the solid-state material is assembled into a rock-salt crystal structure.

22. The solid-state material of claim 21, wherein the solid-state material comprises a face centered cubic structure.

23. The solid-state material of claim 22, wherein the cubic structure has a lattice parameter of about 21.7 Å.

24. A method of forming a solid-state material comprising:
a) dissolving a metal chalcogenide molecular cluster in toluene;
b) dissolving a carbon cluster in toluene; and
c) combining the metal chalcogenide molecular cluster and the carbon cluster to form a solid-state material comprising a solid-state compound having the formula:

[Cluster1][Cluster2]$_n$, wherein
Cluster1 comprises one of $Co_6Se_8(PEt_3)_6$, $Cr_6Te_8(PEt_3)_6$, and $Ni_9Te_6(PEt_3)_8$;
Cluster2 comprises the carbon cluster;
n is the number of Cluster2 clusters in the solid-state compound and n is greater than or equal to 1; and
Cluster1 and Cluster2 are arranged in a binary assembly by charge transfer to form the solid-state material.

25. The method of claim 24, further comprising decanting a supernatant after combining the metal chalcogenide molecular cluster and the carbon cluster.

26. The method of claim 25, further comprising washing a remaining solid with toluene after decanting.

27. The method of claim 26, further comprising drying the remaining solid under vacuum after washing.

28. The method of claim 27, wherein the drying comprises drying for about 12 hours.

* * * * *